United States Patent
Mohr et al.

(10) Patent No.: US 9,179,839 B2
(45) Date of Patent: Nov. 10, 2015

(54) METHOD FOR DETERMINING AT LEAST ONE DIAGNOSIS OR RISK ASSESSMENT PARAMETER RELATED TO AMD

(71) Applicant: Carl Zeiss Meditec AG, Jena (DE)

(72) Inventors: Thomas Mohr, Jena (DE); Elke Machalett, Jena (DE); Martin Hacker, Jena (DE); Martin Kühner, Bad Klosterlausnitz (DE)

(73) Assignee: Carl Zeiss Meditec AG, Jena (DE)

( * ) Notice: Subject to any disclaimer, the term of this patent is extended or adjusted under 35 U.S.C. 154(b) by 116 days.

(21) Appl. No.: 13/891,928

(22) Filed: May 10, 2013

(65) Prior Publication Data
US 2013/0265549 A1     Oct. 10, 2013

(30) Foreign Application Priority Data
Apr. 4, 2012    (DE) .................. 10 2012 007 113

(51) Int. Cl.
*A61B 3/10*     (2006.01)
*A61B 3/00*     (2006.01)
(Continued)

(52) U.S. Cl.
CPC ... *A61B 3/12* (2013.01); *A61B 5/72* (2013.01); *A61B 5/7264* (2013.01);
(Continued)

(58) Field of Classification Search
CPC ...... A61B 5/0059; A61B 5/72; A61B 5/7264; G06T 2207/30041; G06T 7/0028; G01N 2800/163; G06F 19/345
USPC ...................... 351/206, 246; 382/128; 702/19
See application file for complete search history.

(56) References Cited

U.S. PATENT DOCUMENTS 5,016,173 A  *  5/1991  Kenet et al. ................. 382/128
7,058,212 B2 *  6/2006  Schweitzer et al. .......... 382/128
(Continued)

FOREIGN PATENT DOCUMENTS

DE        101 29 652 A1      12/2002
DE    10 2004 042 198 A1      3/2006
(Continued)

OTHER PUBLICATIONS

Kolar, R. Methods for Image Analysis and Pattern Recognition—Application to Early Glaucoma Diagnosis. Vutium BRNO 2009. ISBN 978-80-214-3910-8.*
(Continued)

*Primary Examiner* — Scott J Sugarman
*Assistant Examiner* — Collin X Beatty
(74) *Attorney, Agent, or Firm* — Patterson Thuente Pedersen, P.A.

(57) ABSTRACT

A method for Determining at Least One Parameter for Diagnosis or Risk Assessment of a Disease, including AMD. The distribution of the macular pigment MP of an eye and at least one area A whose bordering line corresponds to a constant optical density MPD and/or concentration MPC of MP is determined by an analysis unit. The bordering line is subjected to a quantitative shape description. At least one parameter DP, suitable for diagnosing a disease and/or the risk of a disease is derived from the quantitative shape description of the bordering line of the areas A. The method is provided for diagnosis or risk assessment but may also be used in the context of treatment of macular pigment deficiency phenomena to select the required supplements. This method, based on the determination of the fractal dimension, is also suitable for diagnosing other diseases such as edemas, actinomycoses, atrophies or lesions.

16 Claims, 4 Drawing Sheets

| Figure | $FD_{min}$ | $FD_{norm}$ | $A_{min}$ | $DP_{div}$ | $DP_{norm}$ |
|---|---|---|---|---|---|
| 1 | 1,01394 | 139 | 28,1 | 4,9 | 0,5 |
| 2 | 1,00488 | 49 | 29,2 | 1,7 | 0,2 |
| 3 | 1,01899 | 190 | 24,9 | 7,6 | 0,8 |
| 4 | 1,04285 | 429 | 8,6 | 49,9 | 5,0 |

(51) Int. Cl.
*A61B 3/12* (2006.01)
*A61B 5/00* (2006.01)
*G06F 19/00* (2011.01)
*G06T 7/00* (2006.01)
*G06T 7/60* (2006.01)

(52) U.S. Cl.
CPC ......... *G06F 19/3431* (2013.01); *G06T 7/0012* (2013.01); *G06T 7/602* (2013.01); *G06T 2207/10101* (2013.01); *G06T 2207/30041* (2013.01)

(56) References Cited

U.S. PATENT DOCUMENTS

| | | | |
|---|---|---|---|
| 7,108,982 B1* | 9/2006 | Hageman | 435/7.1 |
| 7,467,870 B2 | 12/2008 | van de Kraats et al. | |
| 7,467,879 B2 | 12/2008 | Herloski et al. | |
| 7,668,351 B1* | 2/2010 | Soliz et al. | 382/128 |
| 8,078,267 B2 | 12/2011 | Gellerman et al. | |
| 2002/0193948 A1* | 12/2002 | Schweitzer et al. | 702/19 |
| 2005/0010115 A1* | 1/2005 | Bone et al. | 600/476 |
| 2006/0244913 A1* | 11/2006 | Gellermann et al. | 351/205 |
| 2008/0309872 A1* | 12/2008 | Hara et al. | 351/206 |
| 2010/0061601 A1* | 3/2010 | Abramoff et al. | 382/117 |
| 2010/0215223 A1* | 8/2010 | Abe | 382/115 |
| 2010/0241450 A1* | 9/2010 | Gierhart et al. | 705/3 |
| 2011/0026789 A1* | 2/2011 | Hsu et al. | 382/128 |
| 2011/0228219 A1* | 9/2011 | Lee et al. | 351/205 |
| 2012/0150029 A1* | 6/2012 | Debuc | 600/425 |
| 2012/0257164 A1* | 10/2012 | Zee et al. | 351/206 |
| 2013/0114041 A1* | 5/2013 | Iftekharuddin et al. | 351/206 |

FOREIGN PATENT DOCUMENTS

| | | |
|---|---|---|
| DE | 10 2005 058 185 A1 | 6/2007 |
| DE | 10 2007 025 425 A1 | 12/2008 |
| DE | 10 2007 047 300 A1 | 4/2009 |

OTHER PUBLICATIONS

Schmoll, T. Singh, A. Blatter, C. Schriefl, S. Ahlers, C. Schmidt-Erfurth, U. Leitgeb, R. Imaging of the parafoveal capillary network and its integrity analysis using fractal dimension. May 1, 2011 / vol. 2, No. 5 / Biomedical Optics Express.*

Masters, B. Fractal Analysis of the Vascular Tree in the Human Retina. Annu. Rev. Biomed. Eng. 2004, 6:427-52. doi: 10.1146/annurev.bioeng.6.040803.140100.*

Avakian, A. Kalina, R. Sage, E. Rambhia, A. Elliott, K. Chuang, E. Clark, J. Hwang, J.N. Parsons-Wingerter, P. Fractal analysis of region-based vascular change in the normal and non-proliferative diabetic retina. Current Eye Research, 2002, vol. 24, No. 4, pp. 274-280.*

DE Search Report Dated Mar. 18, 2013, cited in DE Application No. 102012007113.2, 5 pages.

Delori et al., "Macular pigment density measured by autofluorescence spectrometry: comparison with reflectometry and heterochromatic flicker photometry", J. Opt. Soc. Am. Am vol. 18, No. 6m Jun. 2001, pp. 1212-1230.

Kaye, "A Random Walk Through Fractal Dimensions, 2$^{nd}$ Edition", Jul. 2008, Copyright © 2000-2014 by John Wiley & Sons, Inc., 427 Pgs.

C. Köhn, Bildanalyse and Bilddaten Kompression, 1996, ISBN 3-446-18503-8, 2 Pgs.

* cited by examiner

| Figure | $FD_{min}$ | $FD_{norm}$ | $A_{min}$ | $DP_{div}$ | $DP_{norm}$ |
|---|---|---|---|---|---|
| 1 | 1,01394 | 139 | 28,1 | 4,9 | 0,5 |
| 2 | 1,00488 | 49 | 29,2 | 1,7 | 0,2 |
| 3 | 1,01899 | 190 | 24,9 | 7,6 | 0,8 |
| 4 | 1,04285 | 429 | 8,6 | 49,9 | 5,0 |

Figure 5

METHOD FOR DETERMINING AT LEAST ONE DIAGNOSIS OR RISK ASSESSMENT PARAMETER RELATED TO AMD

This application claim priority to German Application No.: DE 10 2012 007 113.2, filed Apr. 4, 2012 the entire contents of which are hereby incorporated by reference.

FIELD OF INVENTION

The present invention relates to a method for determining at least one parameter for diagnosis of a disease and/or the risk of developing an age-related macular degeneration (AMD) disease.

BACKGROUND

It is known in the state of the art that macular pigment in particular has a positive effect in preventing AMD because it acts as an absorber for high-energy shortwave radiation and therefore protects the area of sharpest vision from damage. At the same time, macular pigment, containing primarily the carotinoids lutein and zeaxanthin, functions as a radical scavenger. A low optical density of the macular pigment is a risk factor for the development of age-related macular degeneration. Since lutein and zeaxanthin are not formed in the human body but instead must be ingested with food, it is necessary to determine the individual optical density of the macular pigment to detect a possible risk on this basis and to ascertain whether there is a need for supplementation of lutein and zeaxanthin.

For a reliable diagnosis of the disease and/or the risk of developing AMD, it is therefore necessary to determine very accurately and without stray light the density of the macular pigment, which is formed in layers in front of the object to be examined, specifically the ocular fundus. These scattering effects caused by the lens of the eye in particular increase with age, so that the determination of the optical density of the macular pigment on the ocular fundus, which is a known method per se, is increasingly impaired due to scattering effects with the advancing age of the patient. Accurate determination of the optical density of the macular pigment is also important for the decision about the need for and detection of the success of the aforementioned supplementation with lutein and zeaxanthin.

According to the state of the art, it is also known that digital photographs of the retina can be prepared using ophthalmologic instruments, e.g., fundus cameras, ophthalmoscopes or slit lamps. Photographs of the fundus make it possible to determine the optical density of the macular pigment (macular pigment optical density=MPOD or also just MPD).

DE 101 29 652 A1 thus describes one approach in which the ocular fundus is illuminated with light of a wavelength range in which macular pigment has maximum absorption. A shading function is determined from the light intensity that can be measured outside of the macular area (containing no macular pigment). To calculate the optical density of the macular pigment, the quotient of the calculated value of the shading function and the measured intensity value of the light reflected from the illuminated ocular fundus is calculated for each pixel in the area of the macula. The shading function indicates virtually the reflected light that would be reflected by the ocular fundus in the area of the macula if no macular pigment were present.

U.S. Pat. No. 7,467,870 B2 relates to an instrument for highly precise determination of the macular pigment in a patient's eye. The eye is therefore illuminated with a broadband light, and the light reflected by the ocular fundus is then analyzed with the help of a spectrometer. The spectral analysis makes it possible to better differentiate the macular pigment from other light-absorbing substances such as lipofuscin. Since this instrument operates without dilating the pupils, additional measures are necessary to minimize unwanted reflection. In addition to anti-reflection coatings on lenses, a strict separation of the illumination path and the scanning beam path and also an offset arrangement of the lenses are provided in this approach, so that the beam paths additionally pass through the lenses decentrally. According to the setup described in U.S. Pat. No. 7,467,879 B2, measurements are not performed with local resolution but instead are integrated over the illumination and detection area of the retina. It is proposed that the patient's eye should be refocused for peripheral measurements. This makes it possible to determine the lateral distribution of the macular pigment.

It has been found that increased scattering in the eye caused by age-related clouding of the ocular media can lead to a lower measured value for the optical density of the macular pigment. If the light scattering in the lens of the eye also exhibits a great dependence on wavelength, then the density of the macular pigment is calculated as being too high with an increase in scattering even in the two-wavelength fluorescence method ("Macular pigment density measured by autofluorescence spectrometry: comparison with reflectometry and heterochromatic flicker photometry" in Delori et al., J. Opt. Soc. Am. A, Vol. 18, No. 6, June 2001).

Several of the approaches in the state of the art, such as DE 10 2005 058 185 A1, DE 10 2007 025 425 A1 and DE 10 2004 042 198 A1, for example, have been concerned with correctly determining the measured values of the optical density of the macular pigment and/or with the corresponding compensation of the measurement errors.

DE 10 2007 047 300 A1 also describes an approach for accurate reflectometric determination of the optical density of the macular pigment on the ocular fundus without any influence due to interfering light, in particular due to individual light scattering on the anterior ocular media. In addition to measuring the reflected light from illuminated areas of the ocular fundus, the latter is instead illuminated only partially and the intensity of the interfering light from the unilluminated area is measured. This measured value is used as a correction factor in calculating the optical density of the macular pigment.

According to the state of the art, the following parameters are extracted from the measurement of the optical density of the macular pigment, for example:
  mean and maximum concentrations,
  the area and
  the volume of the macular pigment (in the sense of the surface integral of the macular pigment density).

These parameters are used by ophthalmologists in addition to other diagnostically relevant test results to be able to assess the risks of developing a certain disease, e.g., dry AMD and/or to track and assess the course of this eye disease.

SUMMARY OF THE INVENTION

Thus, according to the known state of the art, there is no direct diagnostic correlation based on quantitative data. Existing area considerations of MPD parameters are based in part on pixels and thus depend on the resolution and sensor size of the diagnostic instrument. Treatments with supplements (nutritional supplements) are not currently receiving optimal support through diagnostic statements. Irregularities in the spatial distribution are not evaluated with parameters and cannot be used for diagnostic purposes.

Depending on the method and procedure, the aforementioned parameters are more or less greatly falsified by the extent of a cataract in a patient's eye. Parameters which are preferably influenced as little as possible when a cataract is present are therefore advantageous.

In addition, a rapid analysis and the calculation of diagnostic results that can be allocated unambiguously are advantageous, preferably also in combination with data about clinically known reference variables.

The present invention is based on the problem of developing a method of determining at least one parameter for improved diagnosis or risk assessment of a disease, in particular the risk of developing AMD, which will eliminate the disadvantages of the approaches from the known state of the art. This method should permit a simple, reliable, prompt and reproducible diagnosis without the ophthalmologist having to add important experience for a final diagnosis.

This problem is solved with the proposed method for determining at least one parameter for diagnosis or risk assessment of a disease, in particular the risk of developing AMD in which the distribution of the macular pigment MP in the eye is determined, is achieved by the fact that at least one area whose bordering line corresponds to a constant optical density MPD and/or concentration MPC of the macular pigment is determined by an analysis unit from this distribution of the macular pigment MP.

The bordering line of this area is subjected to a quantitative shape description and at least one shape-describing diagnostic parameter DP is derived, this parameter then being suitable for diagnosing a disease and/or the risk of developing the disease of AMD. The parameter DP is, for example or preferably, a parameter that describes the fractal dimension of the bordering line or a parameter that is obtained as a function of the fractal dimension of the bordering line and additional parameters.

However, the parameter DP may also involve the description of the deviation of the bordering line from the circular shape and/or the similarity to a circular shape. In one possible embodiment, the number of pixels of the bordering line is therefore determined. The number of pixels enclosed by the bordering line is determined and the respective extent of the circle—of the circle having the same area in terms of pixel count is also determined in pixels. The diagnostic parameter DP is then calculated as the ratio of the pixels of the bordering line to the number of pixels of the respective extent of the circle.

In principle, it is also possible to extend the quantitative shape description to the border of the macular pigment density volume (area integral), but that is more complicated numerically.

As an alternative or in addition to the methods proposed above, the problem of determining at least one parameter for diagnosis of a disease and/or the risk of developing AMD, in which the distribution of the macular pigment MP of an eye is determined, is caused by the fact that at least two areas are determined from this distribution of the macular pigment MP by an analysis unit, such that the respective bordering lines of these two areas correspond to a constant optical density MPD, although it varies from one area to another, and/or a constant macular pigment concentration MPC, and these areas are subjected to a relative assessment, and then a parameter DP is derived from this relative assessment of the areas, and this parameter is then suitable for diagnosis of a disease and/or the risk of developing the disease of AMD.

To do so, it is possible to assess shape-describing parameters of the area—such as the fractal dimension or the similarity to the circular shape of the respective bordering lines— as well as the size of the area itself in relation to one another. To do so, ratios of the respective parameters may be formed for different areas. Furthermore, the change in the location of the center of the various areas in relation to one another can be assessed.

Furthermore, the combination with the determination of the quantitative shape description of the fundus autofluorescence signal (FAF) is advantageous in particular when using blue excitation light in the range of 450-495 nm, for example, because this information about the spatial distribution of lipofuscin and thus of position-dependent disturbances in the metabolism of the retina can be taken into account in the quantitative diagnosis. In a preferred embodiment, a diagnostic parameter can also be derived from the border (bordering line) of geographic atrophies in the FAF signal by quantitative shape description or by relative assessment of the areas in relation to one another.

The proposed method is suitable for diagnosis of a disease and/or the risk of developing the disease of AMD, but it may also be used as part of a treatment for targeted, less complicated treatment of deficiency phenomena in the macular pigment in order to select the required supplements and to monitor the success of the treatment through regular and prompt testing.

In principle, the method based on determination of parameters DP, for example, on the determination of the fractal dimension, is also suitable for diagnosing other diseases such as edema, actinomycoses, atrophies or lesions.

Evaluation methods for determining two-dimensional and three-dimensional structures with regard to the determination of fractal dimensions are described, for example, in "A Random Walk through Fractal Dimensions", Brian H. Kaye, Verlag John Wiley & Sons which is incorporated by reference herein.

The determination of the fractal dimensions has the great advantage that this permits scale-invariant quantifications at least in wide areas, i.e., no high demands need be made of certain imaging scales and in particular the results of different measurement instruments are comparable and therefore reliable and reproducible shape descriptions are made possible. It is a particular advantage in determining the fractal dimensions to maintain features when there is an influence of interfering parameters such as a cataract—even in wide areas.

BRIEF DESCRIPTION OF DRAWINGS

The invention is described in greater detail below on the basis of exemplary embodiments, in which:

FIG. 5 shows a tabular overview of parameters DP derived from the fundus photographs according to FIGS. 1 through 4, which are suitable for diagnosing a disease and/or the risk of developing the disease of AMD.

DETAILED DESCRIPTION

Figure 4:
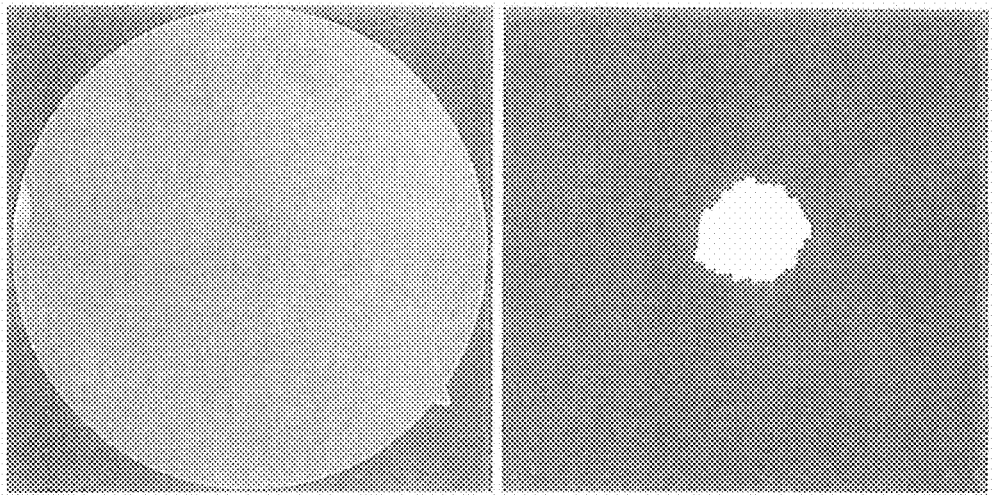
FIG. 4 shows a fourth fundus photograph and the extracted area $A_{min-4}$.

In the method according to the invention, the distribution of the macular pigment MP in the eye is determined for determining at least one parameter for diagnosis of a disease and/or the risk of developing the disease of AMD. An analysis unit determines from this distribution of the macular pigment MP at least on area A whose bordering lines correspond to a constant optical density MPD and/or concentration MPC of the macular pigment MP. The bordering line is subjected to a quantitative shape description. At least one parameter DP derived from the quantitative shape description of the bordering lines of the area A is suitable for diagnosing a disease and/or the risk of developing the disease of AMD.

For the method according to the invention, it is irrelevant how the determination of the distribution of the macular pigment MP in the eye is performed. The position resolution in combination with the wavelength-specific identification of the macular pigment can be implemented by the following, for example:

- a position-resolving, e.g., scanning spectrometer with non-monochromatic illumination or
- a position-resolving area sensor in combination with spectrally selective detection filters and non-monochromatic illumination or
- a position-resolving sensor in combination with spectrally selective, optionally sequential illumination or
- a spectrally resolving device for optical coherence tomography (OCT).

In the determination of the optical density MPD and/or concentration MPC of the macular pigment MP, a background intensity which corresponds to the value of zero d.u. (density units) is always determined, such that the respective areas of the fundus contain negligible amounts of the macular pigment.

In areas with macular pigment, the intensity of the backscattered light is diminished accordingly.

In a first embodiment (I) of the method, the analysis unit determines an area A whose bordering line has a constant optical density MPD and/or concentration MPC of macular pigment MP. The bordering line may be characterized by an optical density MPD and/or concentration of MPC of macular pigment MP between the minimally measurable value and the maximally measured value. A first area $A_{min}$ whose bordering line corresponds to the minimally detectable optical density $MPD_{min}$ and/or concentration $MPC_{min}$ of macular pigment MP is preferred.

The size of this area $A_{min}$ is an important diagnostic parameter, such that a small area $A_{min}$ is an important early indicator of a possible disease-related change.

The area A and therefore also $A_{min}$ at the fundus are preferably to be given in units of degrees of angle of view×degree of angle of view or simply degree×degree. For a round area whose radius appears at a small angle α, this therefore yields an area of $(\pi * \alpha^2)$. For the case of macular pigment, round areas and small angles α are given in first approximation.

Comparative values for real areas can be found in the technical clinical literature. As an example, reference may be made here to the article by F. C. Delori et al.: "Macular pigment density measured by autofluorescence spectrometry: comparison with reflectometry and heterochromatic flicker photometry" in J. Opt. Soc. Am., A, Vol. 18, No. 6, June 2001. This literature describes, for example, an MPD distribution which documents a typical area $A_{min}$ with a radius of approx. 3° of angle of view. This corresponds to an area of 28 deg².

Now if there are areas $A_{min}$ with a much smaller area A than 28 deg² in the patient's eye typically <10 deg²—then this is a first important indication of a possible disease-related change.

Furthermore, FIGS. 1 through 4 show fundus photographs recorded with blue lighting and the areas $A_{min}$ which were extracted therefrom and whose bordering lines correspond to the minimally detectable optical density $MPD_{min}$ of the macular pigment MP.

Figure 1:
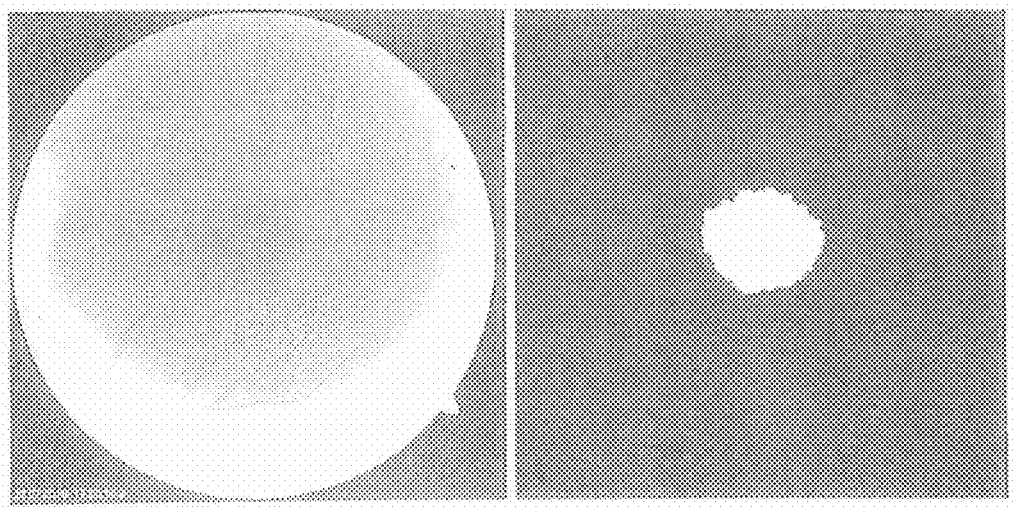
FIG. 1 shows a first fundus photograph and the extracted area $A_{min-1}$.
Figure 2:
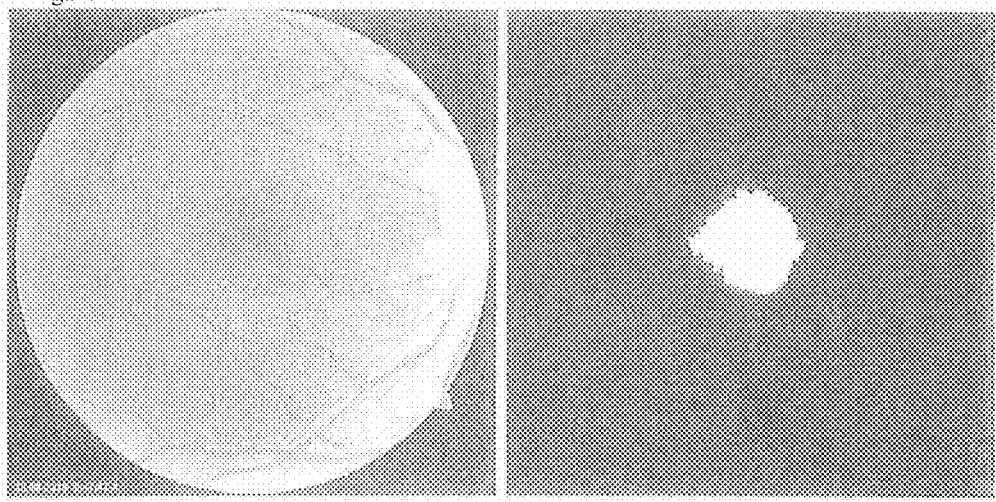
FIG. 2 shows a second fundus photograph and the extracted area $A_{min-2}$.

Although the fundus photograph in FIG. 1 is relatively dark and has a relatively large area $A_{min-1}$=28.1 deg², FIG. 2 shows a relatively bright fundus photograph also with a relatively large area $A_{min-2}$=29.2 deg². Since neither fundus photograph reveals anything unusual and since both have almost circular areas, there is no sign of a disease-related change here.

Figure 3:
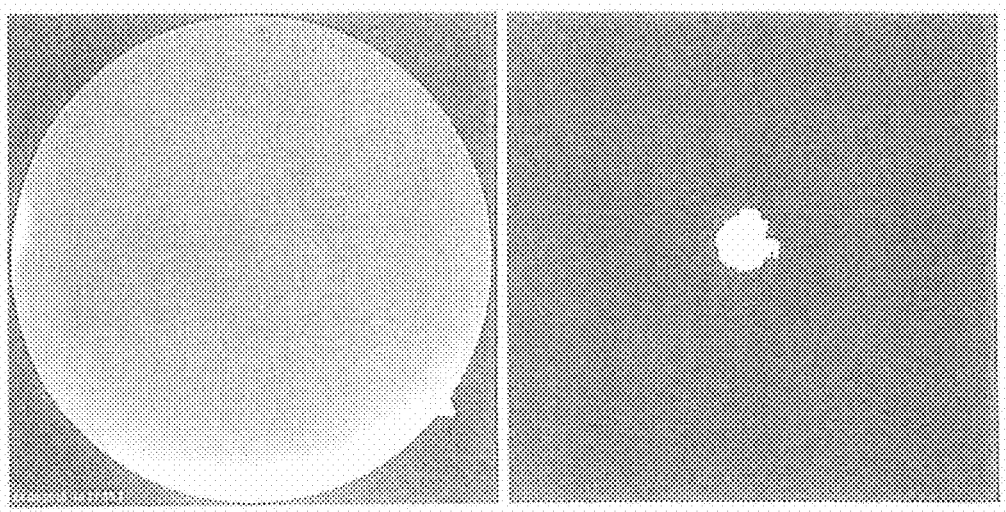
FIG. 3 shows a third fundus photograph and the extracted area $A_{min-3}$.
Figure 6:
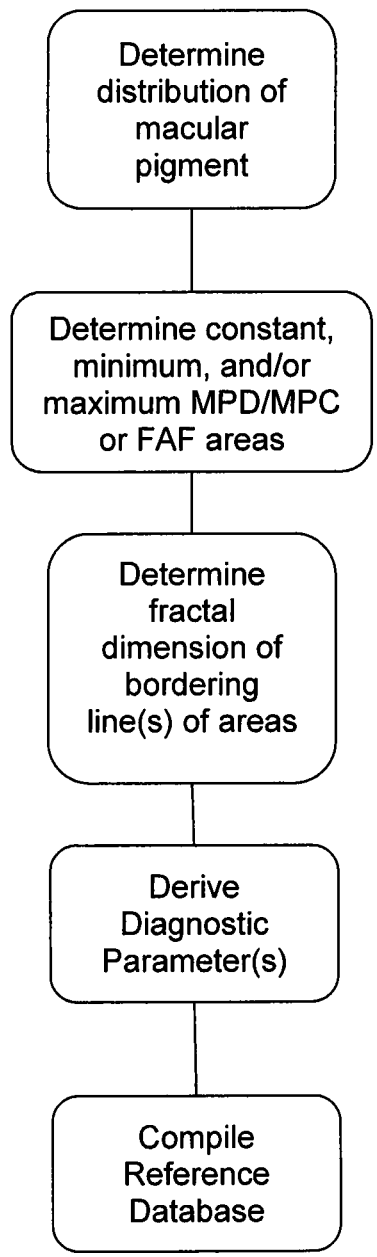
FIG. 6 depicts a flowchart of an embodiment of the claimed method.

The situation is similar with the fundus photograph in FIG. 3, which also has a relatively large area $A_{min-3}$=24.9 deg², shows nothing unusual and has an almost circular area without any major deviations from the circular shape. Thus, here again, there is no sign of a disease-related change.

In contrast with that, FIG. 4 shows a fundus photograph with a relatively small area $A_{min-4}$=8.6 deg² which also has an unusual finding in the form of a pronounced "spike" (on the right) that is indicative of a disease-related change.

In an example embodiment of the method, the fractal dimension is used for a quantitative description of shape of the bordering line of the area A. However, the deviation from a circular shape or the similarity to a circular shape can also be used.

A fractal dimension for the bordering line of the area A of FD>1.03 corresponds to a high measure of fissuring and is indicative of a disease-related change.

Also preferred is the determination of the quantitative shape description of the bordering line of the area $A_{min}$. A fractal dimension of FD>1.03 in particular is indicative of a disease-related change.

Reference is again made to FIGS. 1 to 4 as an example, showing the fundus photographs and the areas $A_{min}$ extracted from them. The following values for the fractal dimensions of the bordering lines of areas $A_{min}$ are obtained for the fundus photographs of FIGS. 1 to 3:

$FD_{min-1}$=1.01394

$FD_{min-2}$=1.00488

$FD_{min-3}$=1.01899

These values confirm that there is no sign of a disease-related change.

The value for the fractal dimension $FD_{min}$ obtained for the fundus photograph according to FIG. 4 in contrast with the preceding is:

$FD_{min-4}$=1.04285 which here again confirms the indication of a disease-related change.

The fractal dimension FD here represents a measure of the fissuring of the bordering line of an area A. The greater the fissuring, the greater is the fractal dimension FD. A great deal of fissuring—and thus a large fractal dimension FD—is an important indicator of a possibly disease-related change.

The fractal dimension FD can therefore also be regarded as an additional parameter DP for diagnosing a disease and/or the risk of developing the disease of AMD. The selectivity of the statement for diagnosis of a disease and/or the risk of developing the disease of AMD can be further increased in this way.

To do so according to another example embodiment of the method, a suitable parameter $DP_{div}$ is derived in which the value of the fractal dimension FD is divided by the respective size of the area A. This yields the ratio of the fractal dimension of the bordering line to the size of the area as follows:

$DP_{div}$=FD/A

The parameter $DP_{div}$ can be determined for areas with bordering lines with different optical densities MPD and/or concentrations MPC of the macular pigment MP. In addition to the parameter $DP_{div-min}$ (determined by dividing the fractal dimension $FD_{min}$ by the area $A_{min}$), the parameters $DP_{div-med}$ and $DP_{div-high}$ which are determined accordingly are also of great interest.

According to an especially preferred embodiment of the method, the standardized fractal dimension $FD_{norm}$ is determined according to the following procedure for diagnosing a disease and/or the risk of developing the disease of AMD:

$$FD_{norm} = (FD-1)*10,000$$

where FD corresponds to the respective fractal dimension of the bordering line of a corresponding area in $\deg^2$. The parameters $FD_{norm-min}$, $FD_{noml-mcd}$ and $FD_{norm-high}$ can be calculated and the diagnostic parameters $DP_{div}$ and $DP_{norm}$ DP can be derived by starting from the predetermined areas $A_{min}$, $A_{med}$ or $A_{high}$.

For example, FIG. 5 shows a table summarizing the parameters $DP_{norm}$ which are derived from the fundus photograph according to FIGS. 1 to 4 and are suitable for diagnosis of a disease and/or the risk of developing the disease of AMD.

The table overview contains lists the figures by number in the first column, i.e., FIGS. 1 to 4.

Column 4 shows the areas $A_{min}$ extracted from the fundus photographs, while columns 2 and 3 show the fractal dimensions FD determined for the bordering lines of these areas. Column 2 contains the fractal dimensions $FD_{min}$ determined for the extracted areas $A_{min}$ and column 3 contains the fractal dimensions $FD_{norm}$ derived from the former and standardized according to the procedure described above:

$$FD_{norm} = (FD_{min}-1)*10,000$$

The parameters $DP_{div}$ contained in column 5 were determined according to the procedure described above by dividing the value of the fractal dimension FD by the respective size of the area A. In the present case, this equation is as follows:

$$DP_{div} = FD_{norm}/A_{min}$$

The standardized parameter $DP_{norm}$ calculated from these given values according to the following equation is shown in column 6:

$$DP_{norm} = DP_{div}/10$$

This column shows that the last row is significantly different from the first three rows. Although these standardized parameters $DP_{norm}$ are below the value 1, row four has a value of $DP_{norm} = 5.0$, which without a doubt indicates a disease-related change.

The standardized parameter $DP_{norm}$ is thus especially suitable for diagnosis of a disease and/or the risk of developing the disease of AMD.

To decide beyond which value of $DP_{norm}$ a disease-related change can be deduced, a corresponding limit value is set. This limit value is approx. 2.5 in the present case.

According to another preferred embodiment of the method, the derived parameters $DP_{div}$ and/or $DP_{norm}$ which are suitable for diagnosing a disease and/or the risk of developing the disease of AMD, as well as the parameters previously determined for assessing them are used to compile a reference database. The reference database naturally also includes the corresponding diagnostic results.

Such a reference database has the advantage that limit values or ratios to be stipulated can be made more specific by a number of available data so that the reliability in diagnosing a disease and/or the risk of developing the disease of AMD can be greatly increased. The reference database may additionally be supported with a normative or general database.

The selectivity of the result for diagnosis of a disease and/or the risk of developing the disease of AMD can for example, be increased by a multi-parameter diagnosis by combining directly disease-related parameters, in particular the diagnostic parameters mentioned above.

In an alternative or supplementary embodiment II of the method, at least one additional area is determined besides a first area A. Thus, for example, in addition to the first area $A_{min}$, one or more additional areas $A_{med}$ and/or $A_{high}$ are determined, where $A_{med}$ and/or $A_{high}$ is/are characterized by a bordering line at the mean optical density $MPD_d$ and/or at an optical density $MPD_{high}$ corresponding to 50-90% of the value of the maximum optical density $MPD_{max}$.

The situation is similar for the mean concentration $MPC_{med}$ and/or the concentration $MPC_{high}$ corresponding to 50-90% of the value of the maximum concentration $MPC_{max}$ of the macular pigment MP.

Another indication of a possible disease-related change occurs when the respective area contents of the areas $A_{min}$, $A_{med}$ and/or $A_{high}$ of an eye deviate from a predetermined ratio, i.e., the area size ratio, of two of the area contents to one another.

A healthy eye has an almost exponential distribution of the macular pigment MP (see, for example, "Macular pigment density measured by autofluorescencc spectrometry: comparison with reflectometry and heterochromatic flicker photometry" in Delori et al., J. Opt. Soc. Am. A, Vol. 18, No. 6, June 2001), so that its distribution forms circular areas A of different diameters.

The specification derived from this for the ratio of the areas $A_{min}:A_{med}$ amounts to approx. 3:1 for the following diameter: $A_{min}$ with approx. 6 degrees and $A_{med}$ with approx. 2 degrees.

Thus, for example, the area contents of the areas $A_{min}$, $A_{med}$ and/or $A_{high}$ would be almost the same in a disease-related change in the form of a three-dimensional needle-shaped distribution of the macular pigment MP and thus would have a different area size ratio.

Another indication of a possible disease-related change occurs when the qualitative shape description of the bordering lines of the areas $A_{min}$, $A_{med}$ and/or $A_{high}$ of an eye differ from a predetermined self-similarity ratio.

As already mentioned, a healthy eye has an almost exponential distribution of macular pigment MP, so that the areas $A_{min}$, $A_{med}$ and/or $A_{high}$ all have a circular bordering line—and are therefore also very self-similar and have almost the same fractal dimension FD.

If there is a circular area $A_{min}$ and an elliptical area $A_{med}$, the result is a different ratio of self-similarity. Deviations in the fractal dimension of $\Delta\_FD > 0.03$ are indicative of a great deviation in the self-similarity and thus provide an indication of a possible disease-related change.

In another embodiment (III), another parameter DP suitable for diagnosing a disease and/or the risk of developing the disease of AMD can be derived from the shape of the areas $A_{min}$, $A_{med}$ and/or $A_{high}$. To do so, it is first necessary to determine the centers of the areas $A_{min}$, $A_{med}$ and/or $A_{high}$. If a great deviation in the position of the centers of the areas compared to one another $A_{min}$, $A_{med}$ and/or $A_{high}$, this also is indicative of a disease-related change. The deviation in the position of the centers can be determined, for example, by calculating the absolute distance of the positions of the centers to one another or to the absolute distance of the positions based on the radius of a circle having the same area as the area $A_{min}$.

It is known in the state of the art that the areas A containing the macular pigment MP can be increased and their fissuring (fractal dimension FD) can be reduced by taking food supplements such as lutein and zeaxanthin.

In addition, the ratio of the areas $A_{min}:A_{med}$ and/or $A_{high}$ can also be altered by supplementation. Thus a hill-shaped distribution in which $A_{min}$ is much larger than $A_{med}$ can develop out of a needle-shaped distribution in which the two areas are comparatively small and are almost the same size.

In addition it is known that supplements with different compositions are available on the market. An individual increase in the macular pigment is made possible depending on the combination of active ingredient. This is manifested in one or more of the diagnostic parameters mentioned above and makes it possible to monitor the treatment accordingly.

Thus the treatment of macular pigment deficiency phenomena can be controlled and monitored in a targeted manner. The supplements are to be selected so that the diagnostic parameters approximate the target specifications as accurately as possible and preferably also very rapidly. In addition, unnecessary doses of supplements can be prevented if the target values have been reached or if saturated is discernible during the follow-up.

With the approach according to the invention, a method for determining at least one parameter for diagnosing a disease and/or the risk of developing the disease of AMD is proposed, permitting a simple, reliable, prompt and reproducible diagnosis.

The diagnosis is supported objectively on the basis of a quantitative shape description of the distribution of the macular pigment. The new parameters described may preferably also be used to create a reference database with a high reproducibility.

This simple, reliable, prompt and reproducible diagnosis also makes it possible to select suitable treatment parameters and to monitor the success of the treatment, which is of increasing importance in particular in a targeted and individually adjusted choice of supplements.

To perform the method according to the invention, the only thing needed is an ophthalmologic instrument for preparing digital fundus images, its control and analysis unit being suitable for extracting the required parameters of the macular pigment from the fundus images.

The approach according to the invention describes a method for improving the reproducibility of the determination of MPD parameters as well as new possibilities of a quantitative description of an MPD distribution for a diagnostic assessment. As a novelty, the fractal dimension of "MPD areas" is determined and additional parameters that have not been described previously are derived.

LIST OF ABBREVIATIONS USED $\alpha$ Angle of view
MP Macular pigment
MPD Optical density of the macular pigment MP
MPC Concentration of the macular pigment MP
$MPD_{max}$ Value of the maximum optical density of the macular pigment MP
$MPC_{max}$ Value of the maximum concentration of the macular pigment MP
$MPD_{min}$ Value of the minimum (detectable) optical density of the macular pigment MP
$MPC_{min}$ Value of the minimum (detectable) concentration of the macular pigment MP
$MPD_{med}$ Value of the mean optical density of the macular pigment MP
$MPC_{med}$ Value of the mean concentration of the macular pigment MP
$MPD_{high}$ Value of the (higher) optical density of the macular pigment MP, corresponding to a value between 50% and 90% of $MPD_{max}$
$MPC_{high}$ Value of the (higher) concentration of the macular pigment MP, corresponding to a value between 50% and 90% of $MPC_{max}$
$A_{min}$ Area whose bordering line corresponds to the minimum detectable optical density $MPD_{min}$ and/or concentration $MPC_{min}$
$A_{med}$ Area whose bordering line corresponds to the mean detectable optical density $MPD_{med}$ and/or concentration $MPC_{med}$
$A_{high}$ Area whose bordering line corresponds to the higher detectable optical density $MPD_{high}$ and/or concentration $MPC_{high}$
$FD_{min}$ Fractal dimension of the bordering line of the areas $A_{min}$
$FD_{med}$ Fractal dimension of the bordering line of the areas $A_{med}$
$FD_{high}$ Fractal dimension of the bordering line of the areas $A_{high}$
$FD_{norm}$ Standardized parameter of the fractal dimension FD
$\Delta\_FD$ Deviations between two fractal dimensions
DP Parameter for diagnosing a disease and/or the risk of developing the disease of AMD
$DP_{div}$ Parameter for diagnosing a disease and/or the risk of developing the disease of AMD created by dividing the area by the value of the respective fractal dimension
$DP_{norm}$ Standardized parameter for diagnosing a disease and/or the risk of developing the disease of AMD

The invention claimed is:

1. A method for determining at least one parameter for diagnosing or assessing the risk of a disease, including the risk of developing the disease of Aging related Macular Degeneration (AMD), the method comprising:
   determining a distribution of the macular pigment MP of an eye;
   determining at least one area whose bordering line corresponds to a constant optical density MPD and/or concentration MPC of the macular pigment by an analysis unit from the distribution of the macular pigment MP; and
   subjecting the at least one area to a quantitative shape description by determining a fractal dimension FD of the bordering line as a standardized value FDnorm, wherein the fractal dimensions FD or FDnorm are indicative of a disease-related change when a predetermined limit value is exceeded; and
   deriving at least one parameter DP which is suitable for diagnosing a disease and/or the risk of developing the disease of AMD and/or monitoring its treatment from the quantitative shape description of the bordering line of the area.

2. The method according to claim 1, further comprising determining the similarity and/or deviation in the bordering line from a circular shape for a quantitative shape description of the at least one area.

3. The method according to claim 1, further comprising determining an area Amin whose bordering line corresponds to the minimally detectable optical density MPDmin and/or concentration MPCmin of the macular pigment by application of the analysis unit.

4. The method according to claim 3, further comprising, in addition to a shape description of the area, using a size of the area itself as the parameter DP.

5. The method according to claim 3, further comprising deriving a parameter DPdiv suitable for diagnosing a disease and/or the risk of developing the disease of AMD in which the value of the fractal dimension FD of the bordering line is divided by the size of the area A.

6. The method according to claim 5, further comprising determining the parameter DPdiv as a standardized value DPnorm.

7. The method according to claim 5, wherein the parameter DPdiv and/or DPnorm thus determined is indicative of a disease-related change when a predetermined limit value is exceeded.

8. The method according to claim 6, using the derived parameter DPdiv and/or DPnorm suitable for diagnosing the disease and/or the risk of developing the disease of AMD to compile a reference database.

9. A method for determining at least one parameter for diagnosing or assessing the risk of a disease, including a risk of the disease of AMD, the method comprising:
   determining the distribution of the macular pigment MP of an eye;
   determining at least two areas by application of an analysis unit from the distribution of the macular pigment MP, their respective bordering lines corresponding to a constant optical density MPD and/or concentration MPC of the macular pigment that is constant but is different from one area to the next, the at least two areas including a first area Amin, and a second area Amed, the bordering line of the second area Amed being determined based on the value of the maximum optical density MPDmax and/or concentration MPCmax, that corresponds to the mean detectable optical density MPDmed and/or concentration MPCmed of the macular pigment;
   subjecting the areas to a relative assessment among one another; and
   deriving a parameter DP suitable for diagnosing a disease and/or the risk of the disease of AMD and/or monitoring its treatment from the relative assessment of the areas among one another.

10. The method according to claim 9, further comprising determining an area Ahigh whose bordering line of a detectable optical density MPDhigh and/or concentration MPChigh corresponds to between 50% and 90% of the value of the maximum optical density MPDmax and/or concentration MPCmax of the macular pigment MP instead of or in addition to the second area Amed.

11. The method according to claim 9, further comprising determining a distribution of fundus autofluorescence signals (FAF) and subjecting the distribution of fundus autofluorescence signals to a quantitative shape description or a relative area assessment, and deriving at least one parameter DP from the quantitative shape description of the MP and the FAF signal, which is suitable for diagnosing a disease and/or the risk of a disease.

12. The method according to claim 10, further comprising designating great differences infractal dimensions for FDmin, FDmed and/or FDhigh of the compared areas Amin, Amed and/or Ahigh as indicative of a disease-related change.

13. The method according to claim 10, further comprising designating great differences in the similarity of the areas Amin, Amed and/or Ahigh or great differences in a degree of deviations from the circular shape indicative of a disease-related change.

14. The method according to claim 11, wherein the parameter DP is suitable for diagnosing AMD and/or the risk of AMD.

15. The method according to claim 13, further comprising determining respective area contents of the areas Amin, Amed and/or Ahigh in the quantitative shape description, such that deviations from a predetermined ratio of the two area contents are indicative of a disease-related change.

16. The method according to claim 13, further comprising determining centers of the areas Amin, Amed and/or Ahigh in the quantitative shape description, such that great deviations in the positions of the centers are indicative of a disease-related change.

* * * * *